US008092838B2

(12) United States Patent
Ohia et al.

(10) Patent No.: US 8,092,838 B2
(45) Date of Patent: Jan. 10, 2012

(54) USE OF HYDROGEN SULFIDE IN THE TREATMENT OF EYE DISEASES

(75) Inventors: Sunny Edet Ohia, Pearland, TX (US); Catherine Atieno Opere, Omaha, NE (US); Guilin Zhan, Omaha, NE (US); Emmanuel Monjok, Houston, TX (US); Kaustubh Kulkami, Houston, TX (US); Ghislaine E. Kouamou, Missouri City, TX (US)

(73) Assignees: The University of Houston System, Houston, TX (US); Board of Regents of the University of Nebraska, Lincoln, NE (US); Creighton University, Omaha, NE (US)

(*) Notice: Subject to any disclaimer, the term of this patent is extended or adjusted under 35 U.S.C. 154(b) by 270 days.

(21) Appl. No.: 11/918,846

(22) PCT Filed: May 1, 2006

(86) PCT No.: PCT/US2006/016751

§ 371 (c)(1), (2), (4) Date: Feb. 27, 2009

(87) PCT Pub. No.: WO2006/119258

PCT Pub. Date: Nov. 9, 2006

(65) Prior Publication Data

US 2009/0214673 A1 Aug. 27, 2009

Related U.S. Application Data

(60) Provisional application No. 60/675,983, filed on Apr. 29, 2005.

(51) Int. Cl.
*A61K 31/74* (2006.01)
*A61K 31/04* (2006.01)

(52) U.S. Cl. .................................... 424/708; 424/78.04

(58) Field of Classification Search ............... 424/78.04, 424/708

See application file for complete search history.

(56) References Cited

OTHER PUBLICATIONS

Kazuho, Abe, et al., The Possible Role of Hydrogen Sulfide as an Endogenous Neuromodulator, The Salk Institute for Biological Studies, San Diego CA, The Journal of Neuroscience, Feb. 1, 1996 16(3), pp. 1066-1071.

Ko, Eto, et al., Brain Hydrogen Sulfide is Severely Diseased in Alzheimer's Disease, Biochemical and Biophysical Research Communications 293 (2002), pp. 1485-1488.

Teague, B., et al., The Smooth Muscle Relaxant Effect of Hydrogen Sulphide in vitro: evidence for a physiological role to control intestinal contractility, Nature Publishing Group, British Journal of Pharmacology, 2002, vol. 137, pp. 139-145.

Yan, Hui, et al., The possible role of Hydrogen Sulfide on the Pathogenesis of Spontaneous Hypertension in Rats, Biochemical and Biophysical Research Communications, vol. 313, 2004, pp. 22-27.

Geng, Bin, et al., H2S Generated by heart in rat and its effects on cardiac function, Biochemical and Biophysical Research Communications, vol. 313, 2004, pp. 362-368.

Zhong, Guangzhen, et al., The Role of Hydrogen Sulfide Generation in the Pathogenesis of Hypertension in Rats Induced by Inhibition of Nitric Oxide Synthase, Journal of Hypertension, 21(10), 2003 pp. 1879-1885.

*Primary Examiner* — Zohreh Fay
(74) *Attorney, Agent, or Firm* — Jackson Walker L.L.P.

(57) ABSTRACT

Topical administration of a generator of H2S in biological tissues for the treatment of eye disorders, such as glaucoma. NaHS caused a time-dependent decrease in intraocular pressure in normotensive, conscious albino rabbits indicating a similar role for H2S in the regulation of aqueous humor dynamics in animals and humans. H2S donors, NaHS and Na2S, inhibited field-stimulated [3H]NE release from porcine isolated iris-ciliary bodies and produced relaxation of pre-contracted iris muscle strips indicating a pharmacological role for H2S in the anterior uvea. The observation that donors of H2S can alter sympathetic neurotransmission and induce an inhibitory action on iris smooth muscle suggests that this gas has the potential to influence several physiological/pathological processes in the eye. The ability of NaHS or Na2S to inhibit [3H]NE release mimics the well-established action some antiglaucoma drugs (e.g. α2-adrenoceptor agonists, prostaglandins) on sympathetic neurotransmission in the anterior uvea and can be used to reduce IOP in animals and humans.

8 Claims, 12 Drawing Sheets

USE OF HYDROGEN SULFIDE IN THE TREATMENT OF EYE DISEASES

RELATED APPLICATION

This application claims priority to U.S. Provisional Patent Application, Ser. No. 60/675,983, entitled "USE OF HYDROGEN SULFIDE IN THE TREATMENT OF EYE DISEASES," filed on Apr. 29, 2005, the entire content of which is hereby incorporated by reference.

GOVERNMENTAL SPONSORSHIP

None.

BACKGROUND

The present invention relates generally to treatment of eye diseases and more particularly to the treatment of eye diseases, such as glaucoma, with hydrogen sulfide ($H_2S$) containing solution or a salt solution capable or generating hydrogen sulfide in situ.

Glaucoma is a blinding disease of the eye that affects approximately three million people in the United States, with more than 120,000 blind due to the condition. Glaucoma is the $2^{nd}$-leading cause of blindness in the United States. Elsewhere in the world, glaucoma treatment is less available, and glaucoma ranks as a leading cause of blindness just about everywhere. Even if people with glaucoma do not become blind, vision can be severely impaired. When the pressure in the eye (intraocular pressure—IOP) increases to dangerous levels, it damages the optic nerve. This can result in decreased peripheral vision and, eventually, blindness. Glaucoma is similar to ocular hypertension but with accompanying optic nerve damage and vision loss.

Several attempts have been made to decrease the intraocular pressure in the eye as a treatment for glaucoma. One method (the present invention) uses an unlikely substance—hydrogen sulfur ($H_2S$).

$H_2S$ is a colorless gas with a pungent odor that is produced endogenously in mammalian tissues from L-cysteine. $H_2S$ is generated from L-cysteine in a reaction catalyzed by two pyridoxal-5'-phosphate dependent-enzymes, cystathionine β-synthase (CBS; EC 4.2.1.22) and cystathionine γ-lyase (CSE; EC 4.4.1.1). Both CBS and CSE are enzymes of the trans-sulfuration pathway that inter-converts L-methionine and L-cysteine but can also use L-cysteine as an alternative substrate to form $H_2S$. Both CBS and CSE are needed for the production of $H_2S$ in tissues. The expression of CBS and/or CSE is dependent on the tissue under study. For instance, several mammalian cells including those from the brain, liver, kidney, skin and blood have been reported to possess CBS as well as CSE activities.

No activity or expression of CBS was detectable when testing human atrium and ventricles, internal mammary arteries and saphenous veins indicating that this enzyme may not play a major role in generating $H_2S$ in these tissues under physiological conditions.

In contrast, CSE is the main $H_2S$ generation enzyme that has been identified, cloned and expressed in the rat vascular bed and heart. In 1995, Watanabe and co-workers (Proc. Natl. Acad. Sci. USA, 92: 1585-1589) produced a CBS knock-out mouse model that represented the disease, homocysteinemia. Using CBS knock-out mice, Eto and coworkers (2002; Biochem. Biophys. Res. Commun. 293: 1485-1488) also showed evidence that CBS produced the endogenous $H_2S$ in the brain.

In 1989, Goodwin and colleagues (J. Anal. Toxicol. 13: 105-109) developed a highly sensitive method for the measurement of $H_2S$ concentrations in tissues. With the highly sensitive and accurate methodology, the concentration of $H_2S$ has been determined in some biological tissues and fluids. For instance, the physiological concentration of $H_2S$ in brain tissue has been shown to be in the range of 50 μM to 160 μM. In rat and human blood, concentrations of $H_2S$ have been reported to be 50 μM and 10-100 μM.

Because of its high lipid solubility, $H_2S$ easily diffuses across biological membranes. When oxidized, $H_2S$ yields sulfur oxide, elemental sulfur and sulfates and can be hydrolyzed to form a hydrosulfide anion and sulfide ion. Approximately 30% of $H_2S$ exists as the undissociated form while about 60% is in the dissociated form as the hydrosulfide anion at a pH of 7.4.

In the environment, $H_2S$ is the predominant sulfur contaminant of natural gas and is a by-product of sewage treatment and paper pulp mills. $H_2S$ is a component of foodstuffs such as dairy products, cooked meats and human feces and is a product of bacterial and helminth metabolism. The toxic effect of acute or chronic exposure of vertebrates and invertebrates to $H_2S$ is well known.

In the eye, toxicity associated with exposure to lethal concentrations of $H_2S$ is mostly at the mucus membrane level leading to keratoconjunctivitis. Until recently, most studies of the biological actions of this gas have focused on its toxicity. Because there is evidence for in situ formation of $H_2S$ by mammalian cells, attention has now been focused on the potential physiological role of this gas. Based on the relatively high concentrations of $H_2S$ in the brain, this gas has been hypothesized to play a physiological role in the brain and indeed, could be involved in some of the diseases of the central nervous system.

For example, the observation that physiological concentrations of $H_2S$ enhance the activity of NMDA receptors and alter the induction of long term potentiation in the hippocampus led Abe and Kimura (1996; J. Neurosci. 16: 1066-1071) to conclude that endogenous $H_2S$ serves as a neuromodulator in the brain. $H_2S$ has also been implicated in some diseases with an overproduction reported in patients with Downs Syndrome. Eto and coworkers (2002; Biochem. Biophys. Res. Commun. 293: 1485-1488) showed that brain $H_2S$ is significantly reduced in patients with Alzheimer's disease indicating the role of this gas in the pathophysiology of this disease. Apart from the brain, $H_2S$ has been reported to produce pharmacological effects on the cardiovascular system and a direct relaxant action on vascular and non-vascular smooth muscles (reviewed by Moore et al., 2003; TIPS, 24: 609).

Unlike the central nervous and cardiovascular systems, no study has addressed the pharmacological effects of $H_2S$ on intraocular pressure, its potential action on the release and/or availability of neurotransmitters in the anterior uvea or on the direct action of this gas on ocular smooth muscle function. Observation of a significant regulatory action of $H_2S$ on intraocular pressure or its presence in physiological concentrations in the anterior uvea opens up new opportunities in glaucoma and other eye treatment.

It is, therefore, an object of the present invention to provide a method of reducing interocular pressure in the eye by using $H_2S$.

It is well known that exposure to high concentrations of $H_2S$ is lethal in both human and experimental animals. However, by using much lower concentrations, $H_2S$ has been reported to produce a wide range of physiological effects in several species. For instance, $H_2S$ produced negative inotropic effects in rats in both in vivo and ill vitro experiments, an effect that was blocked by glibenclamide, an $K_{ATP}$ channel antagonist. Pharmacological studies of the effect of HIS have utilized sodium sulfide ($Na_2S$) and/or sodium hydrosulfide (NaHS) because of their ability to generate this gas in vivo. There is evidence that at a physiological pH of 7.4, about 30% of sulfide whether derived from gaseous $H_2S$ or one of its alkali salts will exist in the form of $H_2S$, with the anion $HS^-$ consisting of the balance. For instance, NaHS dissociates to form $Na^+$ and $HS^-$ in solution, and then $HS^-$ combines with $H^+$ to form $H_2S$. The use of NaHS as a source of $H_2S$ has been reported to accurately and reproducibly define the concentration of this gas in solution than bubbling $H_2S$ gas. Consequently, both NaHS and $Na_2S$ were employed to generate $H_2S$ in vivo and in vitro.

One of the most extensively studied biological actions of $H_2S$ has been within the central nervous system. Chronic contact of neonatal rats with low concentrations of $H_2S$ has been reported to increase serotonin and norepinephrine concentrations in the cerebellum and frontal cortex. Dello Russo and co-workers (2000; J. Endocrinol. 12: 225-233) found that although NaHS had no effect on basal secretion of corticotrophin-releasing hormone (CRH) from rat hypothalamic explants, $H_2S$ consistently inhibited KCl-stimulated release of CRH. Physiological concentrations of $H_2S$ have also been shown to facilitate hippocampal long term potentiation (LTP) in rats by enhancing the N-methyl-D-aspartate (NMDA)-induced inward current. There is evidence that cyclic AMP may mediate the effect of $H_2S$ on NMDA receptors. In summary, evidence from literature confirms an effect of $H_2S$ on neuronal function A review of the literature revealed that most of the pharmacological studies of the postjunctional actions of $H_2S$ have been on smooth muscles. For example, $H_2S$ has been shown to cause relaxation of pre-contracted rat aortic and uterine smooth muscles, in vitro. In uterine smooth muscle, both L-cysteine and NaHS (used as potential $H_2S$ donors) inhibited spontaneous contractions whereas other related amino acids had no such effect. Zhao and coworkers (2001; EMBO J. 20: 6008-6016) found that a small portion of $H_2S$ induced relaxation in the aorta was dependent on the presence of the endothelium and nitric oxide (NO) and could be mediated by $K_{ATP}$ channels. In gastrointestinal and urogenital smooth muscles, Teague and colleagues (2002; Br. J. Pharmacol. 137: 139-145) showed that NaHS caused a concentration-related relaxation of isolated rabbit ileum and rat vas deferens. NaHS also inhibited the contractile response of the guinea pig and rat ilea preparations to electrical stimulation of intramural nerves. Furthermore, Teague et al. found that effects caused by NaHS were blocked by inhibitors of CSE and CBS confirming that $H_2S$ formed from this compound was responsible for these responses.

In rats, an intravenous bolus injection of $H_2S$ caused a transient decrease in blood pressure, a response that was blocked by pretreatment of animals with $K_{ATP}$ channel antagonists. In a study to establish whether an impaired $H_2S$ pathway was associated with hypertension, Zhong and coworkers (2003; J. Hypertension 21: 1879-1885) induced this disease by treating rats with the NO synthase inhibitor, L-NAME and then administered NaHS or vehicle to two groups of animals. Treatment with NaHS effectively prevented the development of hypertension suggesting that a dysfunction of vascular $H_2S$ pathway was involved in L-NAME induced hypertension. Geng and colleagues (2004; Biochem. Biophys. 313: 362-364) also reported that an intravenous bolus injection of NaHS produced a decrease in central venous pressure in rats. In spontaneously hypertensive rats, Yan and coworkers (2004; Biochem. Biophys. Res. Commun. 313: 22-27) found that exogenous administration of $H_2S$ attenuated the elevation of blood pressure and reduced the structural remodeling of the aorta associated with the development of hypertension. Clearly, the evidence available supports a role for $H_2S$ in the pathogenesis of hypertension in rats.

It is, therefore, an object of the present invention to establish a new therapeutic strategy that applies hydrogen sulfide to the eye to cause a lowering of intraocular pressure.

SUMMARY

A method of treating an eye having an elevated level of intraocular pressure comprising applying topically to the eye an effective amount of a solution, wherein the solution comprises dissolved hydrogen sulfide or a dissolved salt of sulfide, hydrogen sulfide, or a mixture thereof, in a liquid carrier.

Topical administration of a generator of $H_2S$ in biological tissues, NaHS (1%) caused a time-dependent decrease in intraocular pressure in normotensive, conscious albino rabbits indicating a similar role for $H_2S$ in the regulation of aqueous humor dynamics in animals and humans.

$H_2S$ donors, NaHS and $Na_2S$ inhibited field-stimulated [$^3$H]NE release from porcine isolated iris-ciliary bodies and produced relaxation of pre-contracted iris muscle strips indicating a pharmacological role for $H_2S$ in the anterior uvea. The observation that donors of $H_2S$ can alter sympathetic neurotransmission and induce an inhibitory action on iris smooth muscle suggests that this gas has the potential to influence several physiological/pathological processes in the eye. Indeed, the ability of NaHS or $Na_2S$ to inhibit [$^3$H]NE release mimics the well-established action some antiglaucoma drugs (e.g. $\alpha_2$-adrenoceptor agonists, prostaglandins) on sympathetic neurotransmission in the anterior uvea and can be used to reduce IOP in animals and humans.

These data compare the effect different concentrations of two $H_2S$ donors on the release of norepinephrine from sympathetic nerves in the anterior uvea.

Figure 4:
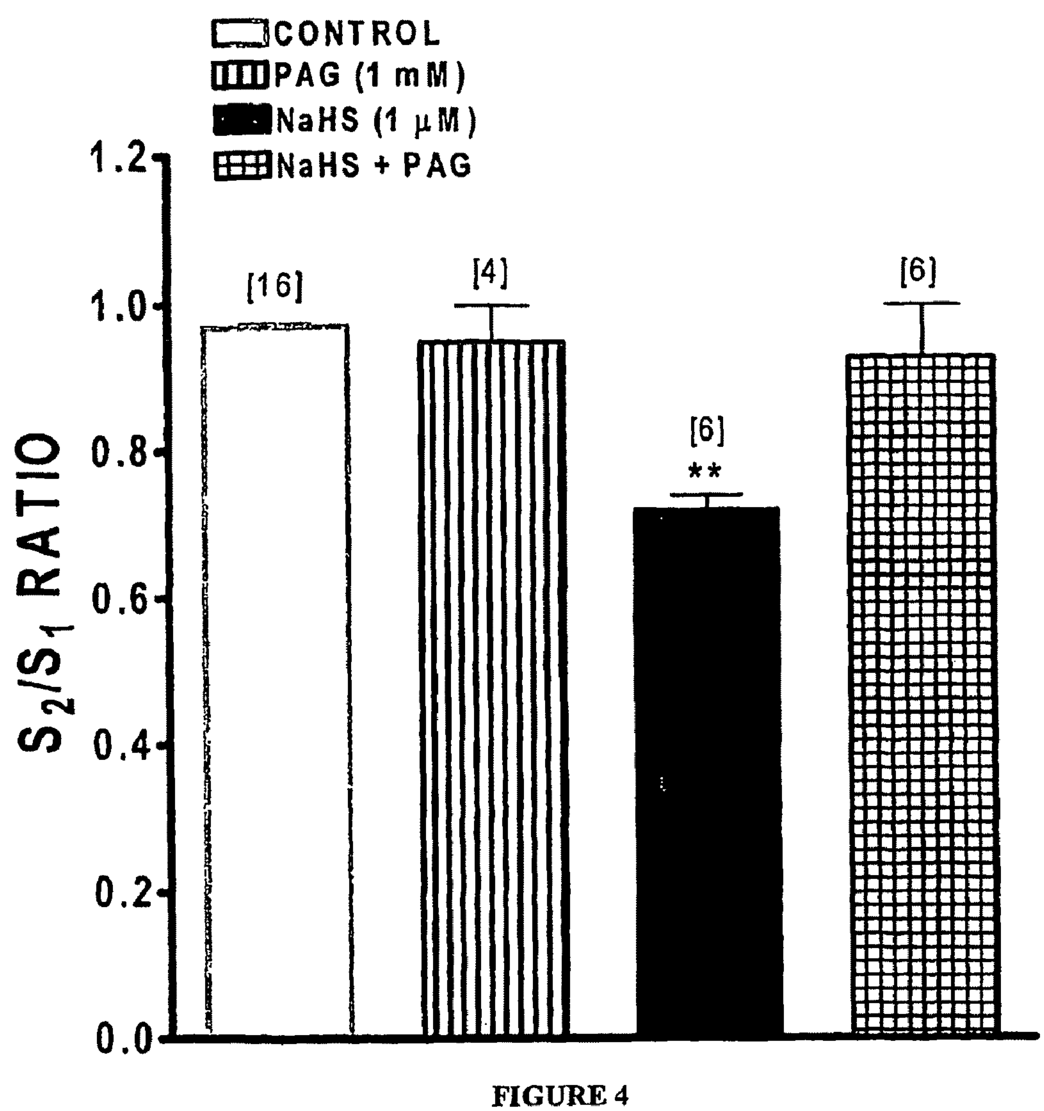

FIG. 4 shows the effect of a propargylglycine (PAG) on NaHS induced inhibition of electrically evoked [$^3$H]NE release from isolated, superfused porcine iris-ciliary bodies: control and in the presence of NaHS (1 μM), PAG (1 mM) and NaHS plus PAG. Vertical bars represent means±S.E.M. **P<0.001, significantly different from untreated controls. These data show that an inhibitor of one of the biosynthetic enzymes of $H_2S$, cystathionine γ-lyase, PAG can reverse the inhibitory action on NaHS on norepinephrine release from sympathetic nerves in the anterior uvea. It confirms that effects caused by NaHS is partially due to biosynthesis of the gas.

Figure 5:
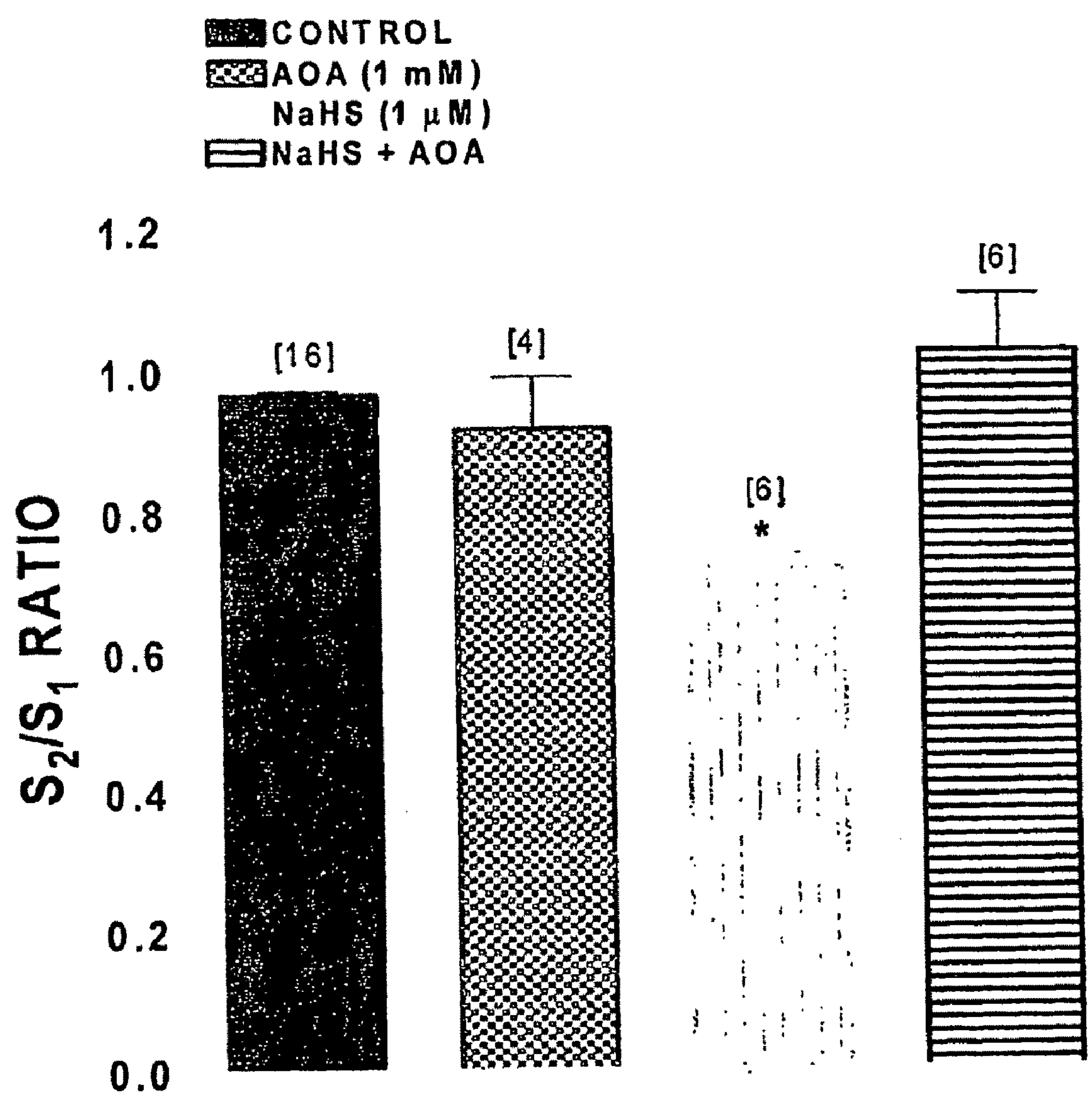

FIG. 5 shows the effect of a aminooxyacetic acid (AOA) on NaHS induced inhibition of electrically evoked [$^3$H]NE release from isolated, superfused porcine iris-ciliary bodies: control and in the presence of NaHS (1 μM), AOA (1 mM) and NaHS plus AOA. Vertical bars represent means±S.E.M. *P<0.01, significantly different from untreated controls. These data show that an inhibitor of one of the biosynthetic enzymes of $H_2S$, cystathionine β-synthase, AOA can reverse the inhibitory action on NaHS on norepinephrine release from sympathetic nerves in the anterior uvea. The data confirm that effects caused by NaHS is partially due to biosynthesis of the gas.

Figure 6:
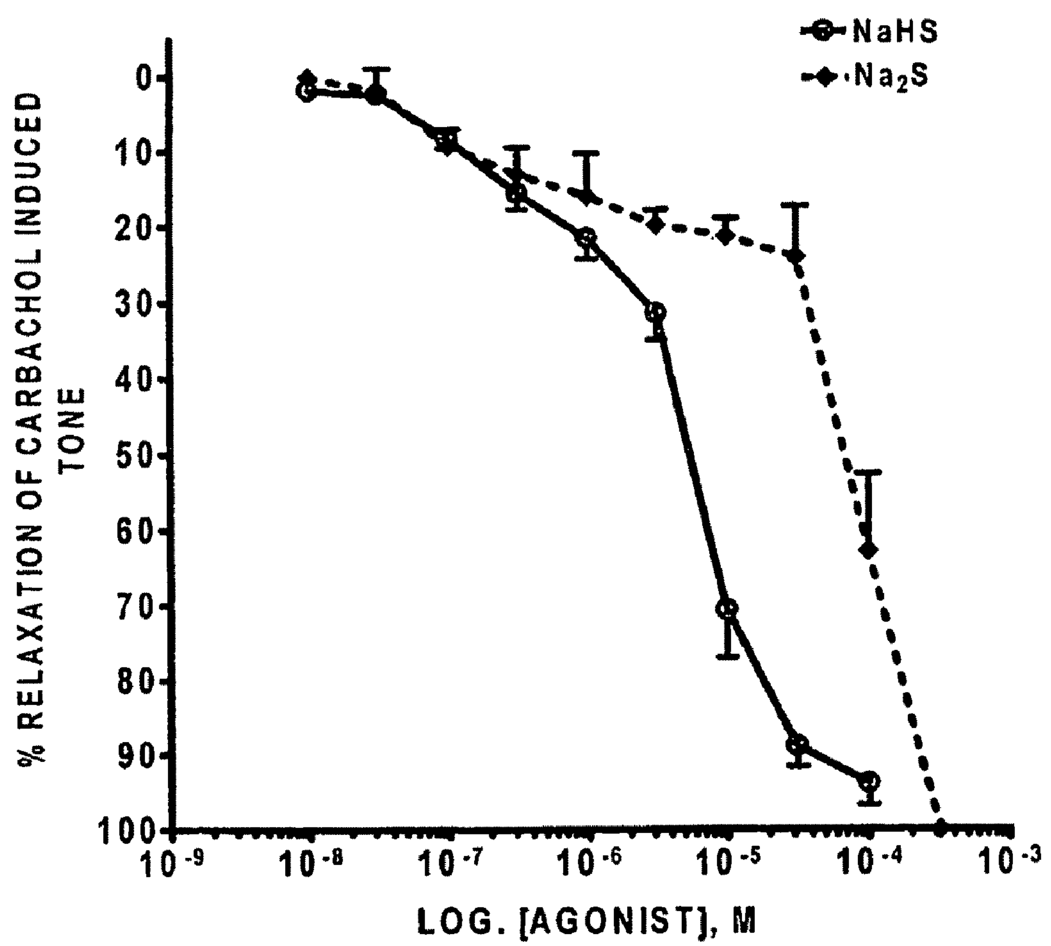

FIG. 6 illustrates the concentration-dependent relaxation of carbachol-induced tone in the isolated porcine iris by NaHS and $Na_2S$. Filled circle=NaHS; Filled diamond=$Na_2S$. Vertical bars represent means±S.E.M. Number of observations is 6-8. These data show that $H_2S$ donors can cause relaxation of porcine iris smooth muscle. NaHS is more potent than $Na_2S$ in eliciting relaxation of tone.

Figure 7:
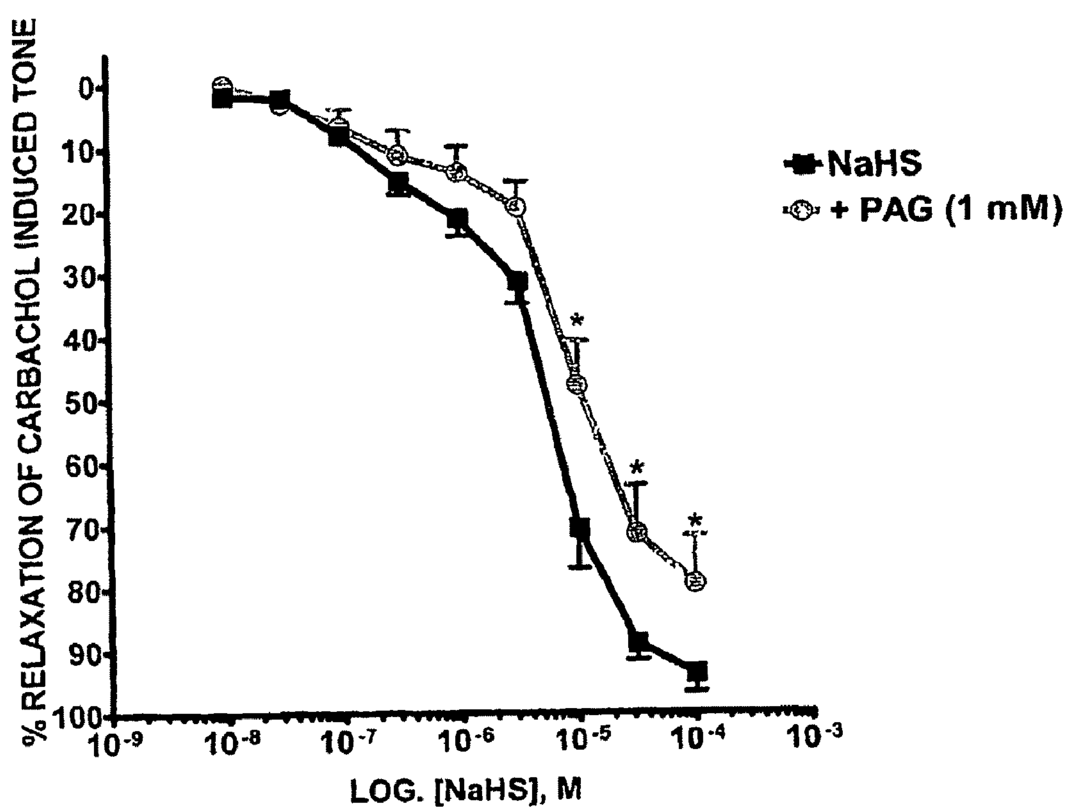

FIG. 7 illustrates the concentration-dependent relaxation of carbachol-induced tone in the isolated porcine iris by NaHS. Filled square=NaHS only; Filled circle=NaHS in the presence of propargylglycine (PAG, 1 mM). Vertical bars represent means±S.E.M. Number of observations is 6-8. *P<0.05, significantly different from NaHS alone. These data show that an inhibitor of one of the biosynthetic enzymes of $H_2S$, cystathionine γ-lyase, PAG can block the relaxation of porcine iris smooth muscle caused by NaHS. The data confirm that effects caused by NaHS is partially due to biosynthesis of the gas.

Figure 8:
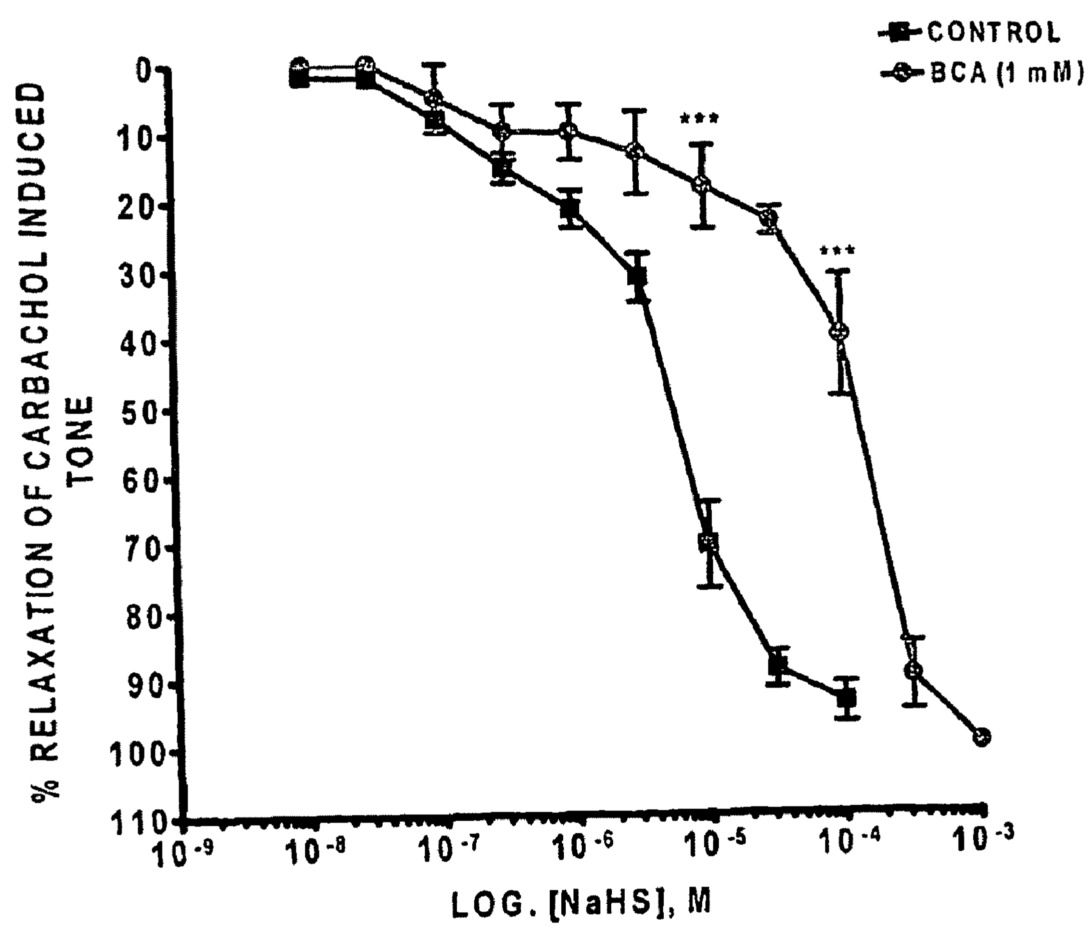

FIG. 8 illustrates the concentration-dependent relaxation of carbachol-induced tone in the isolated porcine iris by NaHS. Filled square=NaHS only; Filled circle=NaHS in the presence of β-cyano-L-alanine (BCA, 1 mM). Vertical bars represent means±S.E.M. Number of observations is 4-6. ***P<0.001, significantly different from NaHS alone. These data show that an inhibitor of one of the biosynthetic enzymes of $H_2S$, cystathionine γ-lyase, BCA can block the relaxation of porcine iris smooth muscle caused by NaHS. The data confirm that effects caused by NaHS is partially due to biosynthesis of the gas.

Figure 9:
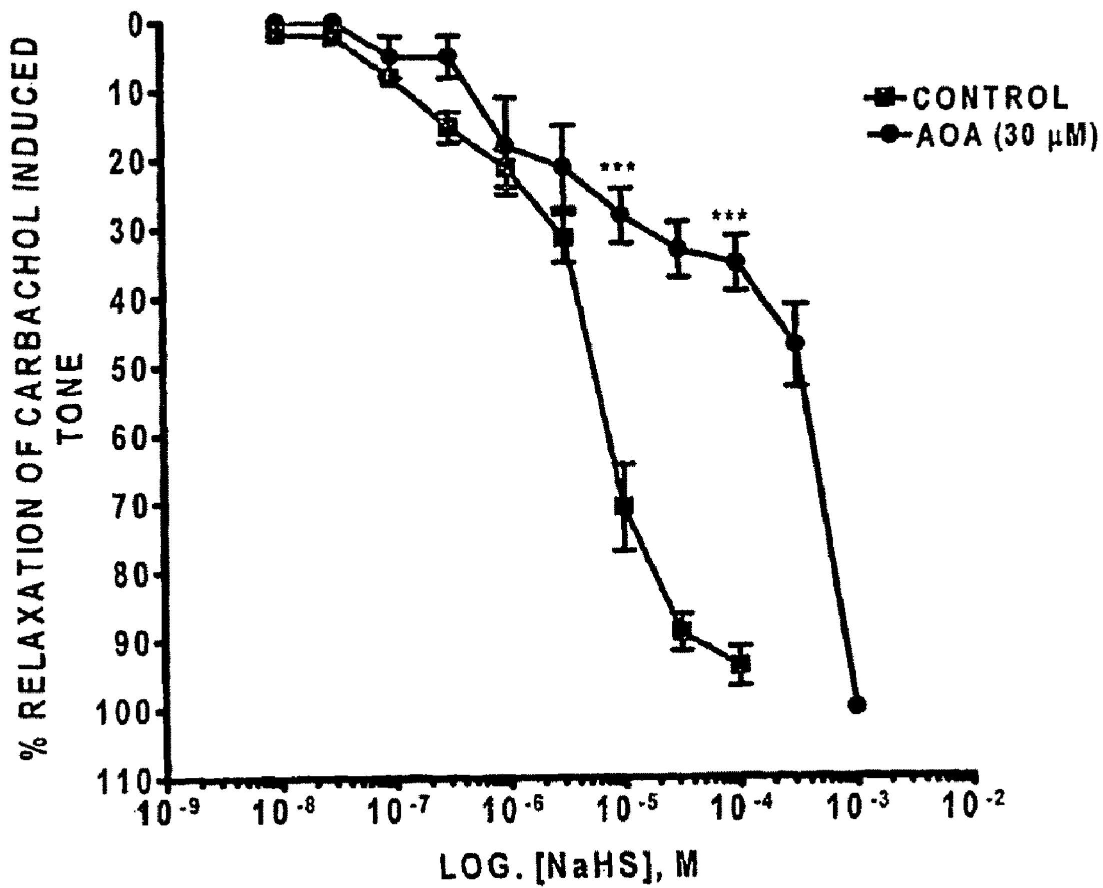

FIG. 9 illustrates the concentration-dependent relaxation of carbachol-induced tone in the isolated porcine iris by NaHS. Filled square=NaHS only; Filled circle=NaHS in the presence of aminooxyacetic acid (AOA, 30 μM). Vertical bars represent means±S.E.M. Number of observations is 6-8. ***P<0.001, significantly different from NaHS alone. These data show that an inhibitor of one of the biosynthetic enzymes of $H_2S$, cystathionine β-synthase, AOA can block the relaxation of porcine iris smooth muscle caused by NaHS. The data confirm that effects caused by NaHS is partially due to biosynthesis of the gas.

Figure 10:
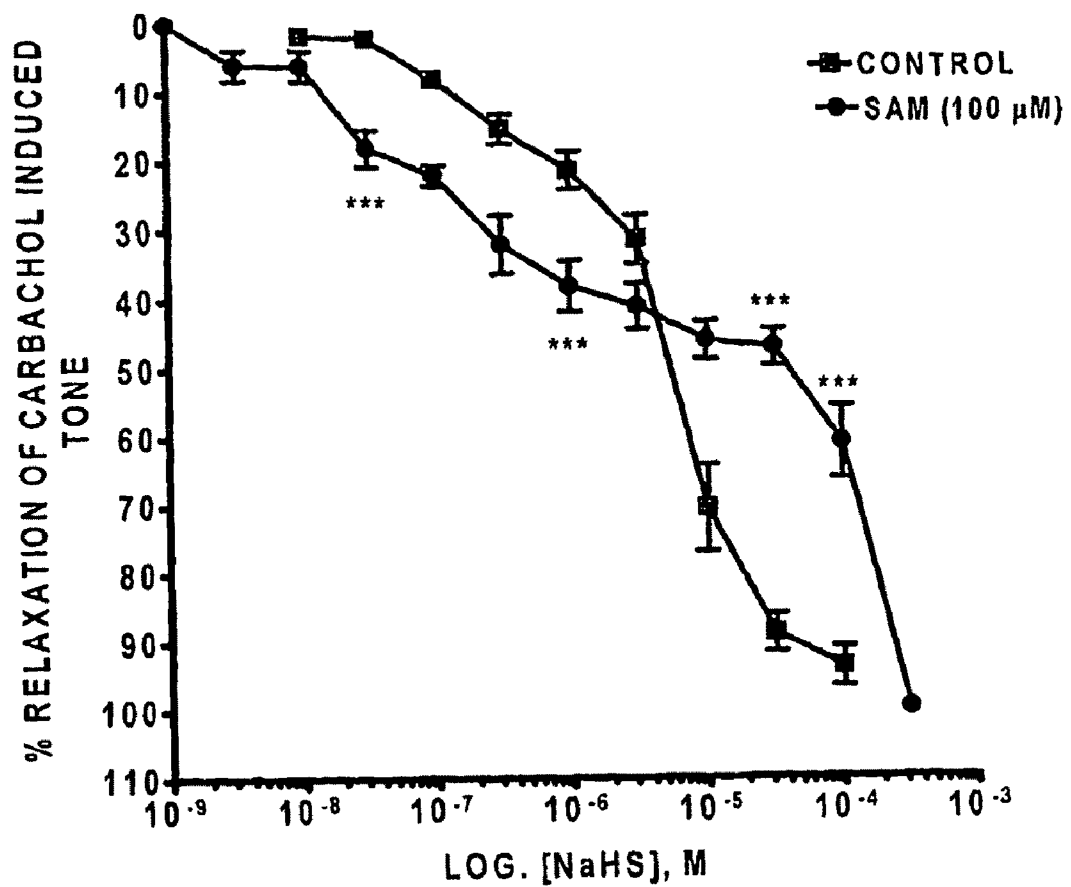

FIG. 10 illustrates the concentration-dependent relaxation of carbachol-induced tone in the isolated porcine iris by NaHS. Filled square=NaHS only; Filled circle NaHS in the presence of S-adenosyl-L-methionine (SAM, 100 μM). Vertical bars represent means±S.E.M. Number of observations is 6-8. ***P<0.001, significantly different from NaHS alone. These data show that an activator of one of the biosynthetic enzymes of $H_2S$, cystathionine β-synthase, SAM can enhance the relaxation of porcine iris smooth muscle caused by low concentrations of NaHS. The data confirm that effects caused by NaHS is partially due to biosynthesis of the gas.

Figure 11:
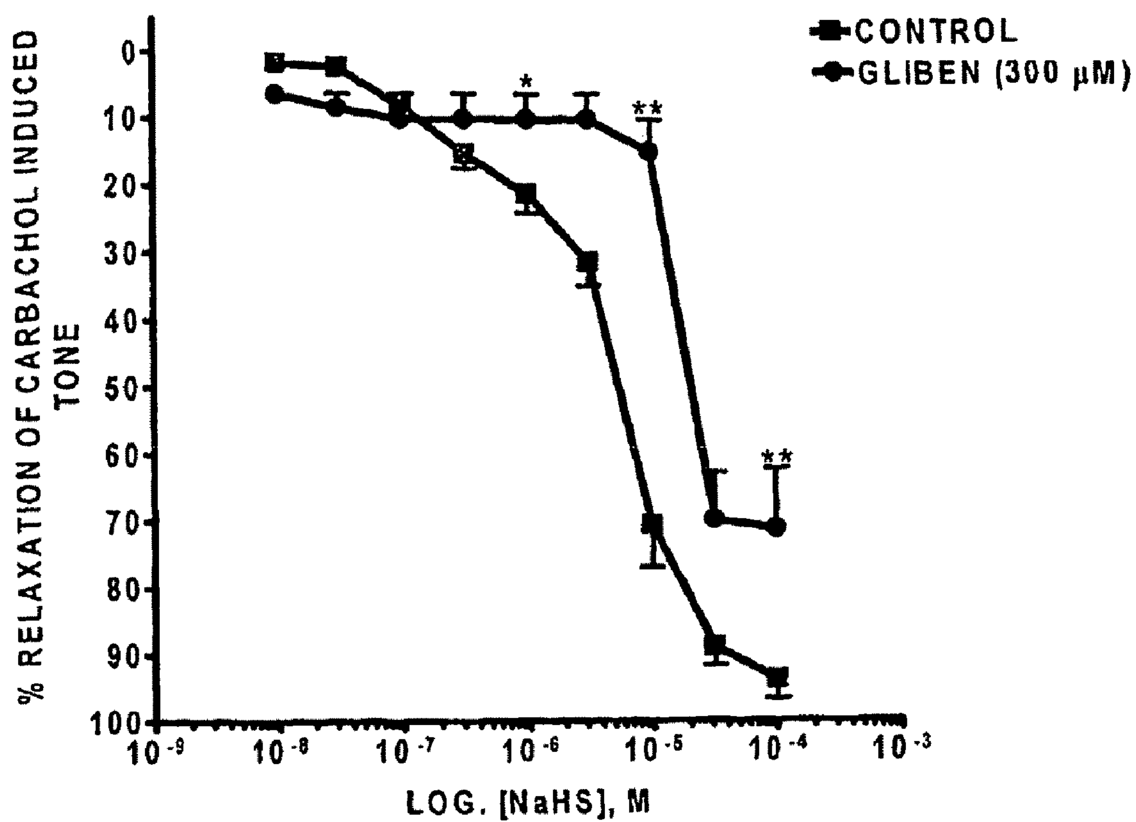

FIG. 11 illustrates the concentration-dependent relaxation of carbachol-induced tone in the isolated porcine iris by NaHS. Filled square=NaHS only; Filled circle=NaHS in the presence of glibenclamide (GLIBEN 300 μM). Vertical bars represent means±S.E.M. Number of observations is 6-8. *P<0.05, **P<0.001, significantly different from NaHS alone. These data confirm that relaxation of porcine iris smooth muscle caused by NaHS involves the activation of $K_{ATP}$ channels. These channels have been implicated the pharmacological action of $H_2S$ gas on biological tissues.

Figure 12:
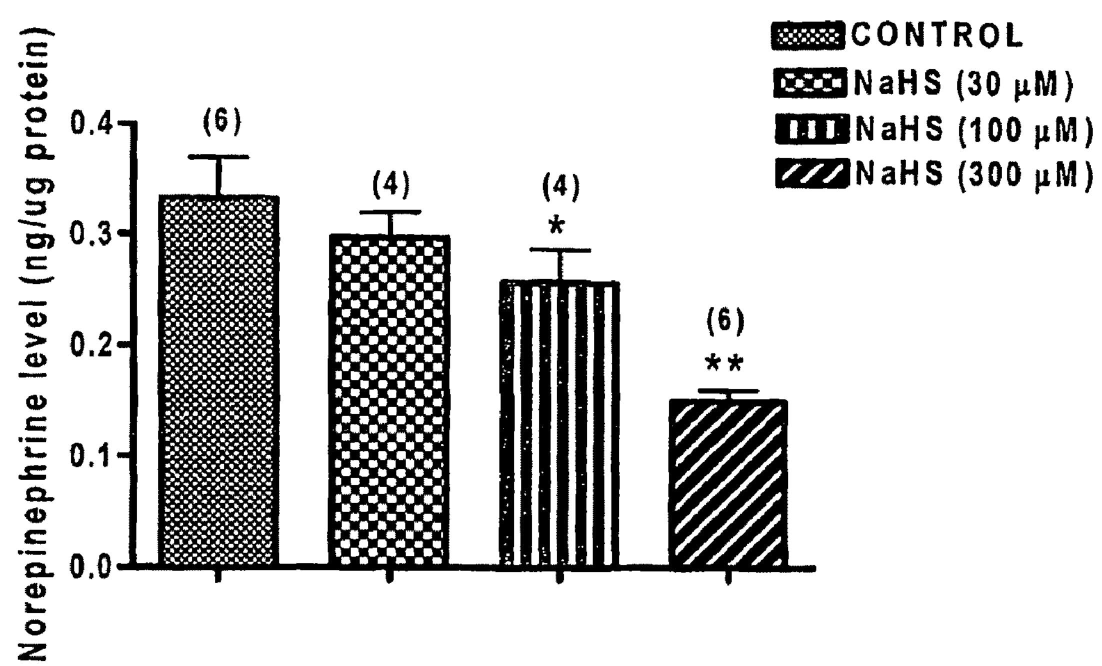

FIG. 12 shows the effect of NaHS on norepinephrine level from isolated porcine iris-ciliary body. Vertical bars represent means±S.E.M. Numbers of observations is in parenthesis. *P<0.05, **P<0.001 significantly different from untreated control. These data confirm that a donor of $H_2S$ can reduce the norepinephrine pool in sympathetic nerves from porcine anterior uvea. The data support results obtained from neurotransmitter release studies which show a decrease in norepinephrine output.

DETAILED DESCRIPTION OF THE PREFERRED EMBODIMENTS

The hydrogen sulfide, $H_2S$, used for this invention can be generated in several ways. One way is to bubble hydrogen sulfide gas into a liquid medium or carrier (such as water, saline, or a physiologically acceptable buffer solution) until saturation. Another way, and the preferred way, is to generate the hydrogen sulfide in situ using a sulfide salt, preferably a water soluble sulfide salt, such as a Group IA salt, including NaHS, $Na_2S$, or its respective K salt, dissolved in a carrier. These salts will dissolve in water readily, and under physiological conditions, $H_2S$ is generated in situ.

Before a carrier solution saturated with gaseous $H_2S$ can be used for this invention, a roughly 10 fold dilution is needed. After this dilution, the effective amount used per eye would be roughly about one drop, which is roughly about 100 microliter. As for the $H_2S$ generated in situ from a salt, the concentration of the final salt solution should range from about 0.01% (weight/volume) to about 4% (weight/volume). The preferred final concentration of the salt solution is about 1% (weight/volume). The effective amount of this 1% (weight/volume) salt solution is about 1 drop per eye.

The application of $H_2S$ can be given to an eye once a day, or up to two to three times a day. The treatments can be repeated the following days if needed. The treatment regiment can consist of: measuring the intraocular pressure after application of the solution; comparing the measured intraocular pressure with the desired level of intraocular pressure; and repeating the applying, measuring and comparing steps until the measured intraocular pressure is at or below the desired intraocular pressure.

Figure 1:
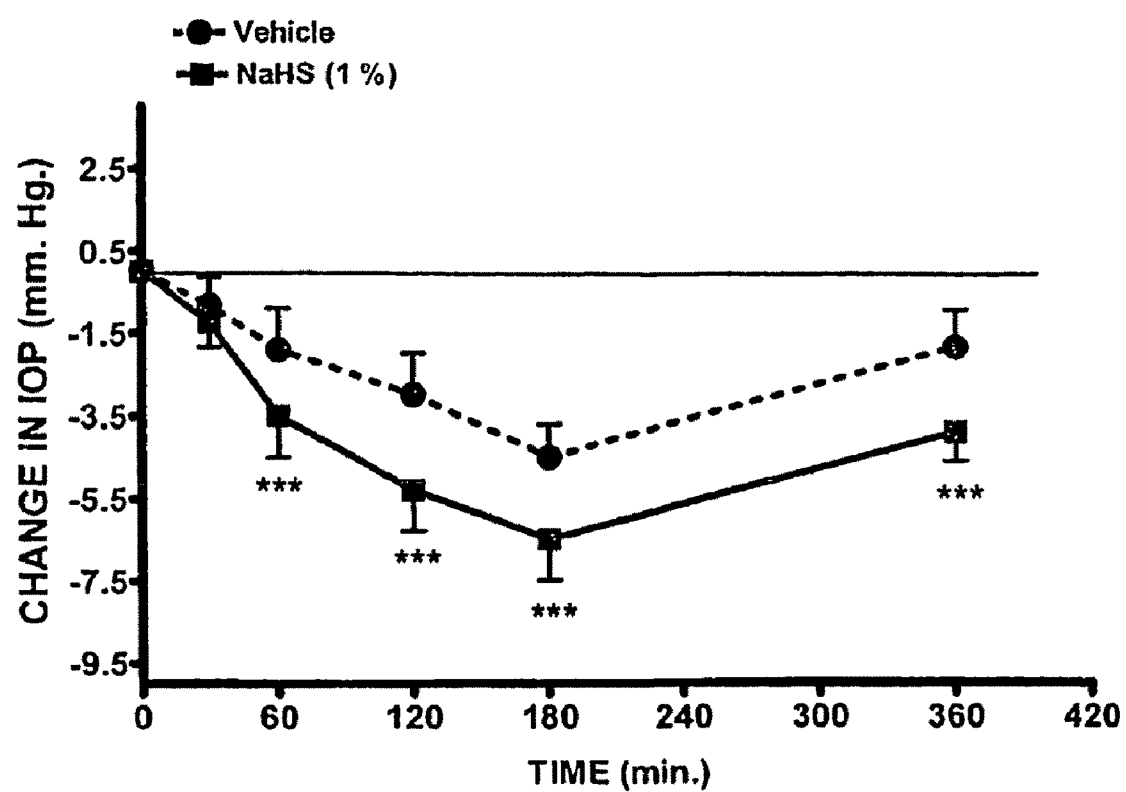
FIG. 1 shows the effect of a generator of $H_2S$ in biological tissues, NaHS on intraocular pressure (IOP) in normotensive, conscious albino rabbits. A 1% dose of NaHS was applied topically to one eye and the saline vehicle to the other eye. Vertical bars represent means± standard error of the mean (SEM) of data obtained from six rabbits. ***$P<0.001$, significantly different from baseline IOP. This data shows that a $H_2S$ donor can cause a drop in IOP in an experimental animal model. It was concluded that pharmacological doses of $H_2S$ can alter aqueous humor dynamics leading to a fall in IOP.

The effect of a generator of $H_2S$ in biological tissues (NaHS) on intraocular pressure in normotensive, conscious albino rabbits was examined. In the eyes of a rabbit, the desired intraocular pressure is around 20 mm Hg. While in human, the desired intraocular pressure in the eye is in the range of from about 12 mm Hg to 15 mm Hg. Ranges of about 18 to 24 mm Hg in a human eye are generally considered elevated. Two baseline intraocular pressure measurements were made in nine rabbits using a pneumatonometer (Medtronic, Model 30 Classic, Jacksonville, Fla.) at −1, and 0 hour after topical application of proparacaine 0.5%. NaHS (1%, dissolved in sterile saline solution) was applied topically to one eye of each animal while the saline vehicle was administered to the other (control) eyes. Intraocular pressures were measured in both eyes at +0.5, +1, +3, and +6 hours after instillation of the drug and vehicle. No hyperemia and/or papillary changes were observed in both experimental and control eyes of rabbits at all tines tested. A dose of NaHS (1%) caused a time-dependent significant ($p<0.001$) reduction in intraocular pressure in the treated eyes that reached a maximum at 3 hours and remained depressed after 6 hours (FIG. 1). A parallel (but smaller) decrease in intraocular pressure was observed in eyes treated with only the saline vehicle (no drug) suggesting that this compound can produce contralateral effects.

The possibilities that $H_2S$ may alter intraocular pressure by reducing the release of norepinephrine from sympathetic nerves supplying the anterior uvea was tested. Currently used anti-glaucoma drugs of the $\alpha_2$-adrenoceptor agonist (e.g. ALPHAGAN) class also decrease the release of norepinephrine from sympathetic nerves in the anterior uvea. The effect of the $H_2S$ generators, NaHS and $Na_2S$ on field-stimulated $[^3H]$-norepinephrine ($[^3H]$NE) release from isolated, superfused porcine iris-ciliary bodies was also studied. The methodology utilized for measuring $[^3H]$NE release was essentially the same employed by Ohia and coworkers (1997; Invest. Ophthalmol. Vis. Sci. 38: 842-847).

Figure 2A:
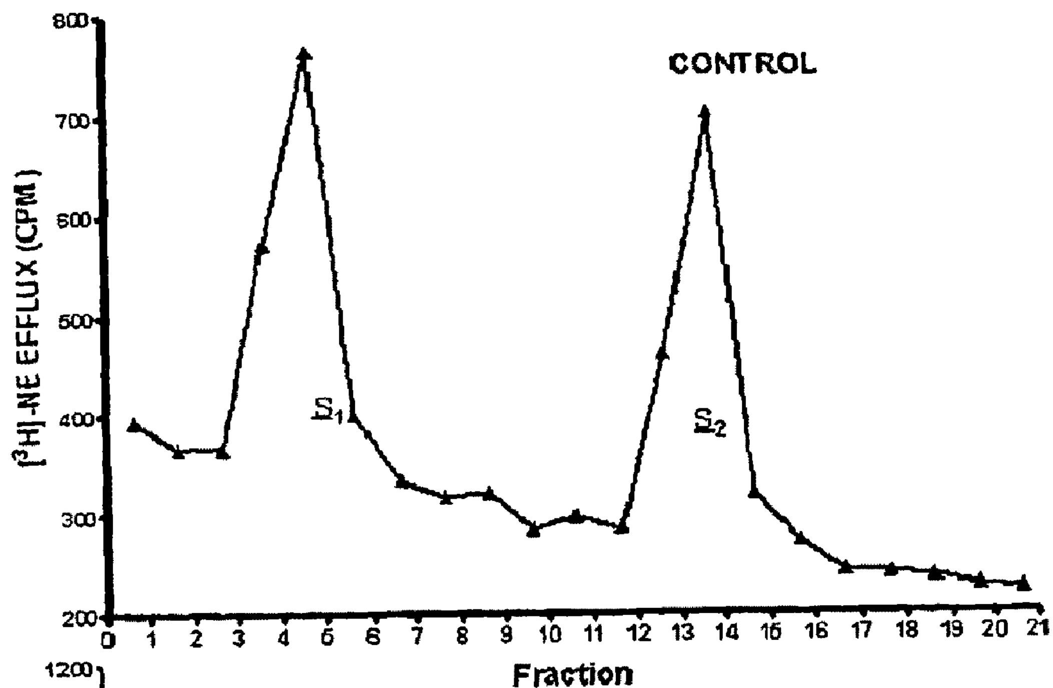
FIGS. 2*a* and 2*b* show the effect of NaHS on field-stimulated [$^3$H]NE release from the isolated, superfused porcine iris-ciliary body. Trains of field stimulation (5 Hz, 2 msec. pulse duration, 12 V, 60 s) were applied at fraction 4 ($S_1$) and fraction 12 ($S_2$). Top Panel, FIG. 2*a*, control (no agents present). Bottom Panel, FIG. 2*b*, NaHS (1 μM) applied 8 minutes before and during $S_2$. Fractions of the superlusate containing [$^3$H]NE were collected at 4 minute intervals and analyzed for radioactivity by liquid scintillation spectrometry. These data illustrate that a $H_2S$ donor can alter the release of norepinephrine from sympathetic nerves in the anterior uvea.
Figure 2B:
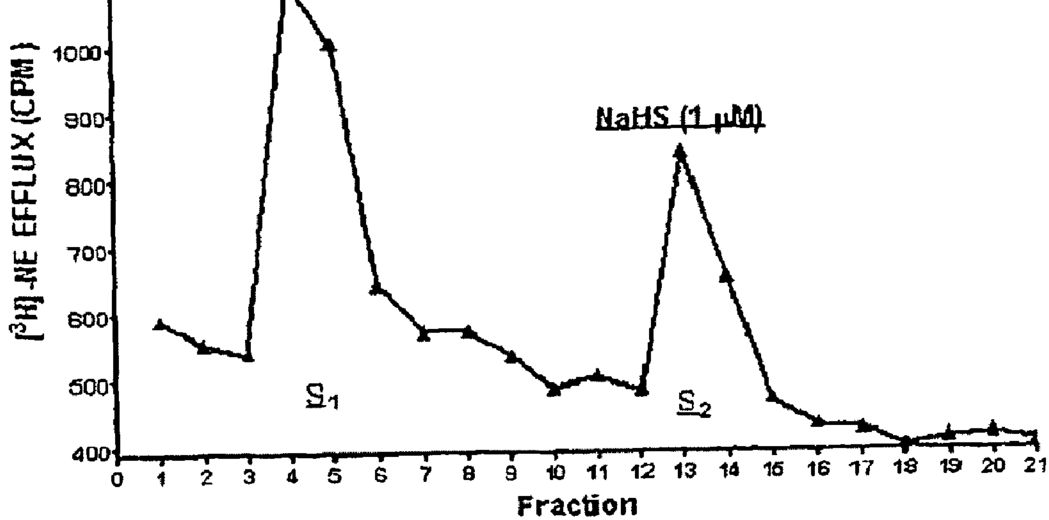
Figure 3A:
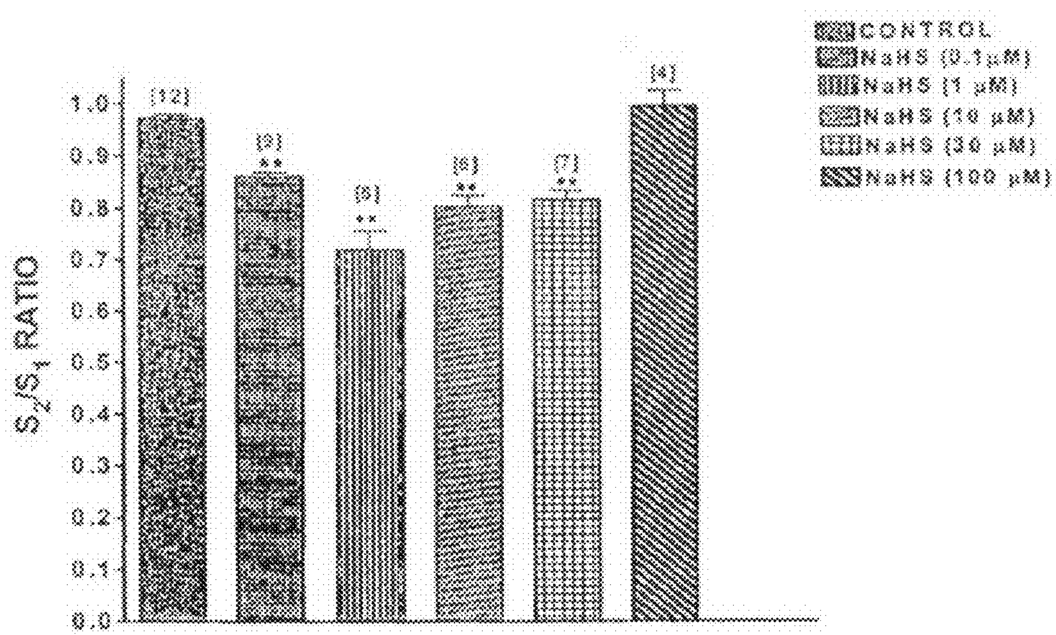
FIGS. 3*a* and 3*b* show the effect of NaHS (top panel, FIG. 3*a*) and $Na_2S$ (bottom panel, FIG. 3*b*) on field-stimulated [$^3$H]NE release from isolated, superfused porcine iris-ciliary bodies: control and in the presence of NaHS (0.1-10 μM) or Na2S (1-100 μM). Vertical bars represent means±S.E.M. Number of observations is in parenthesis. *$P<0.05$, **$P<0.001$, significantly different from untreated control.
Figure 3B:
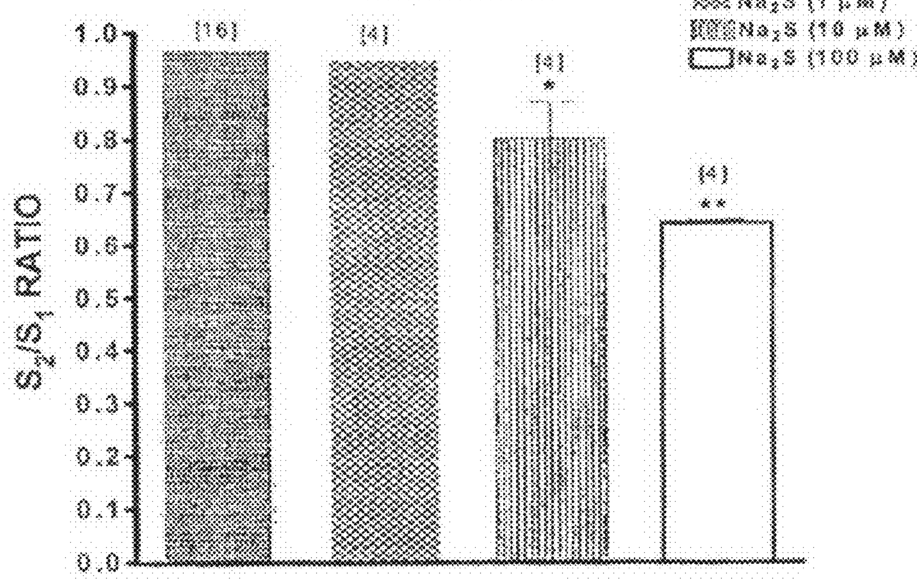

Isolated porcine ICBs were incubated for 60 min. at 37° C. in carbogen-gassed Krebs buffer containing 2.5 μCi/ml [3H] NE. Release of $[^3H]$NE was elicited by 300 d.c. electrical pulses (5 Hz, 2 msec p.d., 60 s, supramaximal voltage). Fractions of the superfusate were collected at 4-minute intervals and analyzed for radioactivity by liquid scintillation spectrometry. All tissues received two stimulations ($S_1$ and $S_2$) 30 min. apart and NaHS or $Na_2S$ was added 8 min. before and during the $S_2$ stimulation period. As illustrated in the example in FIG. 2, application of NaHS (1 μM) 8 minutes before the second train of field stimulation ($S_2$) elicited a marked inhibition of stimulation-evoked $[^3H]$NE release from isolated porcine iris-ciliary bodies. Application of NaHS (0.1-100 μM) caused a concentration-dependent inhibition of electrically-evoked $[^3H]$NE overflow (FIG. 3, top panel).

The pharmacological actions of $H_2S$ using $Na_2S$ as a donor was investigated. $Na_2S$ (1-100 μM) caused a concentration-dependent inhibition of electrically-evoked $[^3H]$NE release without affecting basal tritium efflux (FIG. 3, bottom panel). Data obtained from these studies show that both NaHS and $Na_2S$ can inhibit the release of electrically-evoked $[^3H]$NE from porcine iris-ciliary bodies suggesting that in pharmacological concentrations, $H_2S$ can have a negative regulatory action on sympathetic neurotransmission in this tissue.

Both propargylglycine (PAG, 1 mM; inhibitor of cystathionine γ-lyase) and aminooxyacetic acid (AOA, 1 mM; inhibitor of cystathionine β-synthase) blocked the inhibitory response elicited by NaHS on evoked $[^3H]$NE release (FIGS. 4 and 5). Taken together, these results suggest that the pharmacological action of NaHS on sympathetic neurotransmission in porcine iris-ciliary bodies is dependent, at least in part, on the endogenous biosynthesis of $H_2S$. From the results of these tests, it is concluded that both NaHS and $Na_2S$ can inhibit the release of electrically-evoked [3H]NE from porcine iris-ciliary bodies, an effect that is dependent on the production of $H_2S$ in this tissue.

In another series of experiments, the hypothesis that $H_2S$ can produce a direct relaxant action on iris smooth muscle in vitro was tested. The effect of NaHS on relaxation of tone induced by the muscarinic receptor agonist, carbachol in the isolated porcine irides was examined. The methodology employed for measuring contractile/relaxant activity of the isolated porcine iris was essentially the same employed by Ohia and colleagues (2000; J. Ocul. Pharmacol. Ther. 16: 429-438).

NaHS (30 nM-100 μM) produced a concentration-related relaxation of tone induced by a submaximal concentration of carbachol in the isolated porcine iris (FIG. 4). Isolated porcine iris muscle strips were set up in organ baths containing oxygenated Krebs buffer solution at 37° C. Longitudinal isometric tension was recorded via a grass FT03 Force-displacement Transducer and analyzed using the Polyview computer software. An initial load of 150 mg was placed on each tissue after which they were allowed to equilibrate for one hour. The relaxant action of NaHS or $Na_2S$ on carbachol-induced tone was studied in the absence and presence of inhibitors of cystathionine γ-lyase (propargylglycine, PAG, β-cyanolalanine, BCA), an inhibitor of cystathionine β-synthase (AOA), an activator of cystathionine β-synthase (S-adenosyl-L-methionine, SAM) and $K_{ATP}$ channel antagonist (glibenclamide).

In the concentration range, 30 nM to 300 μM, both NaHS and Na2S caused relaxations of tone induced by a submaximal concentration of carbachol yielding $IC_{50}$ values of 7 μM and 70 μM, respectively (FIG. 6). Both PAG (1 mM) and BCA (1 mM) shifted concentration-response curves to NaHS to the right (FIGS. 7 and 8). Likewise, AOA (30 μM) caused significant ($P<0.001$) rightward shifts of concentration-response curves to NaHS (FIG. 9). In contrast, the activator of cystathionine β-synthase, SAM (100 μM) caused a significant leftward shift of NaHS concentration-response curve at $H_2S$ donor concentrations less than 3 μM (FIG. 10). The relaxations induced by the higher concentration of NaHS were attenuated by SAM (FIG. 10). The $K_{ATP}$ channel blocker, glibenclamide (300 μM) produced a significant rightward shift of concentration-response curves to NaHS (FIG. 11).

In conclusion, both NaHS and $Na_2S$ can elicit inhibitory response in isolated porcine irides, an effect that is dependent on the biosynthesis of $H_2S$ in this muscle. Furthermore, the inhibitory action of NaHS in porcine irides is mediated, at least in part, by $K_{ATP}$ channels. Taken together, these results demonstrate that endogenous generation of $H_2S$ by NaHS or $Na_2S$ relaxes porcine iris smooth muscle, a response that confirms and extends earlier reports in vascular (Zhao et al., 2001; EMBO J. 20: 6008-6016) and gastrointestinal (Teague et al., 2002; Br. J. Pharmacol. 137: 139-145) smooth muscles.

To determine the mechanism of action of $H_2S$ donors on sympathetic neurotransmitter pools in the anterior uvea, the direct effect of NaHS was studied on catecholamine (norepinephrine, epinephrine and dopamine) concentrations in porcine iris-ciliary bodies using High Precision Liquid Chromatography techniques. NaHS (30-300 μM) caused a concentration-dependent decrease in norepinephrine concentrations in the isolated porcine iris-ciliary body (FIG. 12). Data from this study supports the previous observation that $H_2S$ donors can reduce the release of $[^3H]$NE from isolated porcine irides. It appears that by reducing the availability of the neurotransmitter (norepinephrine), $H_2S$ can attenuate sympathetic neurotransmission in porcine anterior uvea.

The ability of $H_2S$ donors, NaHS or $Na_2S$ to alter the release of norepinephrine from sympathetic nerves (in a manner similar to $\alpha_2$-adrenoceptor agonists) could account, at least in part, for the observed IOP lowering action of these compounds in experimental animals. Furthermore, the fact that inhibitors (or activators) of the biosynthetic enzymes for $H_2S$ are involved in the actions of NaHS on both anterior uveal sympathetic nerves and smooth muscle indicates that this gas plays a role in the observed IOP response.

Glaucoma therapy is largely dependent upon the effect of drugs on primary messengers in the sympathetic and parasympathetic nervous system of the anterior uvea. It is thus reasonable that modification of a neurotransmitter output from sympathetic nerves induced by $H_2S$ may account, at least, in part for an effect of this gas on aqueous humor dynamics. Furthermore, data obtained from experiments using $H_2S$ donors confirm that this gas can have a direct relaxant action on ocular smooth muscles that play a role in the regulation of IOP.

It appears that the presence of $H_2S$ in physiologically relevant concentrations in tissue of the anterior uvea can also be involved in the IOP lowering action of some antiglaucoma drugs. Based on the ocular hypotensive action of $H_2S$, it appears that a new class of anti-glaucoma drugs is identified. Because of reported side effects of the different classes of currently used drugs for the treatment of glaucoma, there is a need to identify additional groups of compounds with specific and potent action on this disease.

This discovery can be applied to the use of $H_2S$ in the treatment of glaucoma and other diseases of the eye in animals and humans.

Formulation of $H_2S$ for Lowering of Intracular Pressure $H_2S$ can be applied to the eye in a topical formulation of gas dissolved in a liquid carrier or as agents that can release the gas in physiological medium (e.g., NaHS). Liquid formulations containing different concentrations of the gas can be applied at different dosages until the desired drop in IOP is achieved.

The invention claimed is:

1. A method of treating an eye having an elevated level of intraocular pressure comprising:

applying topically to the eye an effective amount of a solution, wherein the solution comprises dissolved gaseous hydrogen sulfide or a dissolved salt, wherein the salt is $Na_2S$, NaHS, $K_2S$, KHS, or a mixture thereof, in a liquid carrier, and wherein the effective amount of the solution has a concentration that ranges from 0.01% to 1% of the dissolved salt, by weight/volume, in the liquid carrier.

2. The method of claim 1, wherein the liquid carrier comprises water, saline, or a physiologically acceptable buffer.

3. The method of claim 1, wherein the effective amount of the solution has a concentration of 1% of the dissolved salt, by weight/volume, in the liquid carrier.

4. A method of treating an eye having an elevated level of intraocular pressure comprising:

applying topically to the eye an effective amount of a solution, wherein the solution has a concentration that ranges from 0.01% to 1% of a dissolved salt, by weight/volume, wherein the salt is $Na_2S$, NaHS, or a mixture thereof, in a liquid carrier.

5. A method of treating an eye having a level of intraocular pressure that is above a desired level, comprising:

applying topically to the eye an effective amount of a solution, wherein the solution comprises a dissolved gaseous hydrogen sulfide or a dissolved salt, wherein the salt is $Na_2S$, NaHS, $K_2S$, KHS or a mixture thereof, in a liquid carrier, and wherein the solution has a concentration that ranges from 0.01% to 1% of the dissolved salt, by weight/volume, in the liquid carrier;

measuring the intraocular pressure after application of the solution;

comparing the measured intraocular pressure with the desired level of intraocular pressure; and repeating the applying, measuring and comparing steps until the measured intraocular pressure is at or below the desired intraocular pressure.

6. The method of claim 5, wherein the salt is $Na_2S$, NaHS, or a mixture thereof.

7. The method of claim 5, wherein the liquid carrier comprises water, saline, or a physiologically acceptable buffer.

8. The method of claim 5, wherein the effective amount of the solution has a concentration of 1% of the dissolved salt, by weight/volume, in the liquid carrier.

* * * * *